(12) United States Patent
Reimer et al.

(10) Patent No.: US 7,697,199 B2
(45) Date of Patent: Apr. 13, 2010

(54) LIGHTING DEVICE AND OBSERVATION DEVICE

(75) Inventors: Peter Reimer, Ellwangen (DE); Fritz Straehle, Heubach (DE); Daniel Kolster, Oberkochen (DE)

(73) Assignee: Carl Zeiss AG, Oberkochen (DE)

( * ) Notice: Subject to any disclaimer, the term of this patent is extended or adjusted under 35 U.S.C. 154(b) by 165 days.

(21) Appl. No.: 10/965,692

(22) Filed: Oct. 14, 2004

(65) Prior Publication Data
US 2005/0128574 A1   Jun. 16, 2005

(30) Foreign Application Priority Data
Oct. 14, 2003   (DE) ................. 103 47 732

(51) Int. Cl.
*G02B 21/06* (2006.01)
(52) U.S. Cl. ...................... 359/385; 359/389
(58) Field of Classification Search ................. 359/389, 359/385
See application file for complete search history.

(56) References Cited

U.S. PATENT DOCUMENTS

| 4,779,968 A | 10/1988 | Sander |
| 5,126,877 A | 6/1992 | Biber |
| 5,287,129 A * | 2/1994 | Sano et al. .................. 351/233 |
| 5,914,771 A | 6/1999 | Biber |
| 6,011,647 A * | 1/2000 | Geschwentner ............. 359/389 |
| 6,624,932 B2 | 9/2003 | Koetke |
| 2004/0004694 A1* | 1/2004 | Sugino et al. ............... 351/206 |
| 2004/0119941 A1* | 6/2004 | Goldfain et al. ............. 351/205 |

FOREIGN PATENT DOCUMENTS

| DE | 40 28 605 A1 | 3/1992 |
| DE | 196 38 263 A1 | 4/1998 |
| EP | 1 109 046 A1 | 6/2001 |

* cited by examiner

*Primary Examiner*—Joshua L Pritchett
(74) *Attorney, Agent, or Firm*—Kriegsman & Kriegsman

(57) ABSTRACT

A lighting device (40) is described for an observation device (10), in particular for an ophthalmologic operating microscope, as well as such an observation device (10). The lighting device (40) has a light source (41) as well as a number of optical components, which are provided between light source (41) and an objective element (11). The optical components are designed according to the invention in such a way that the imaging of the lighting pupil (43) and the observation pupils is produced on the fundus of the eye (30). In this way, an exactly defined interaction of the lighting beam path (56) with an observation beam path is made possible, whereby practical requirements can be fulfilled relative to the homogeneity of the red reflex with simultaneous sufficiently good contrasting.

22 Claims, 8 Drawing Sheets

FIG 8
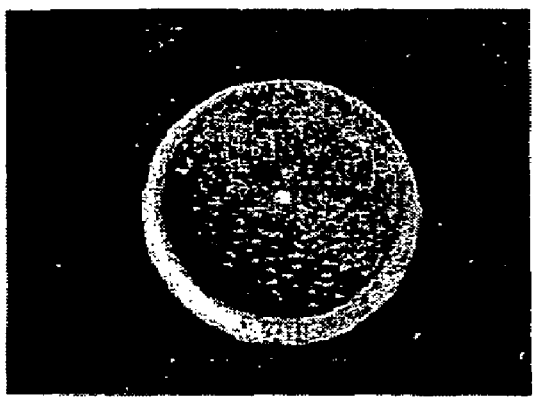 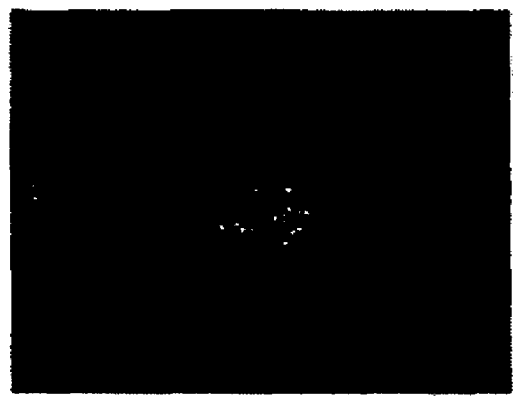
FIG 9
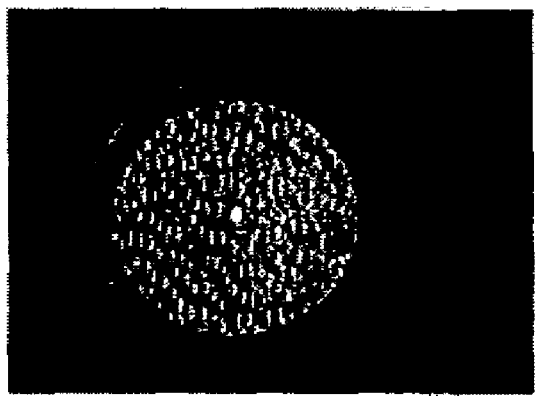 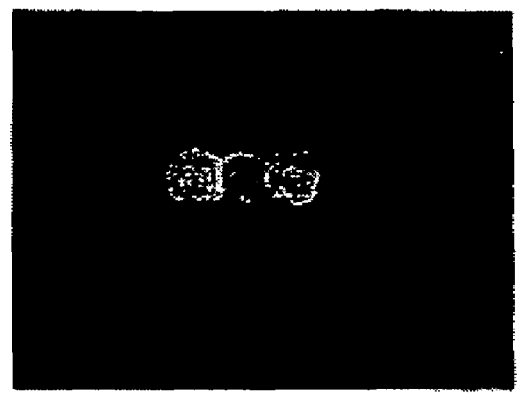
FIG 10
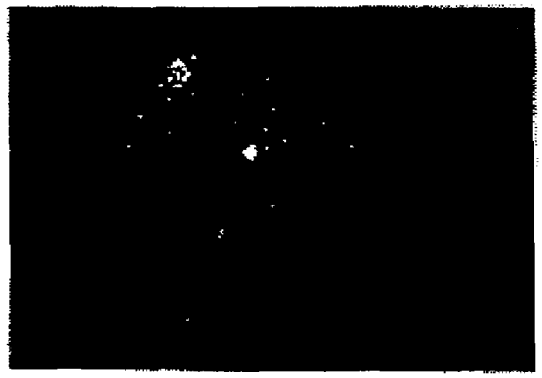 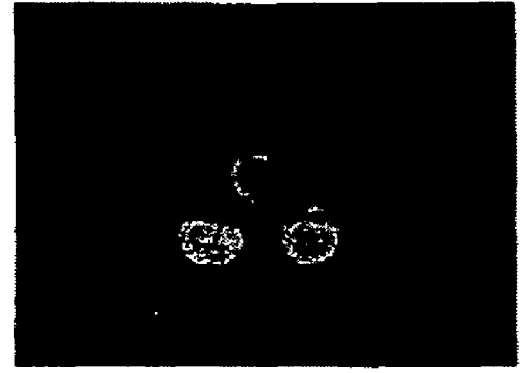

FIG 11
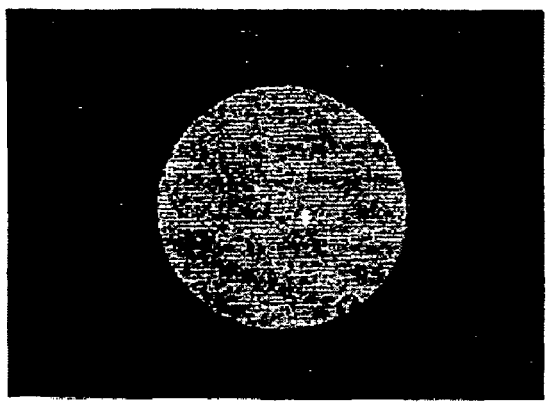
FIG 12

LIGHTING DEVICE AND OBSERVATION DEVICE

BACKGROUND OF THE INVENTION

The present invention relates to a lighting device for an observation device and to an observation device.

For example, an observation device may involve an operating microscope. In particular, the observation device can be designed as an ophthalmologic operating microscope, which is utilized, for example, for a special application in eye surgery, i.e., cataract surgery.

In the case of cataract surgery, a lens of the eye—which is clouded, for example, due to the cataract—is replaced by an artificial lens.

The lens of an eye is found inside a thin envelope, the so-called lens capsule. In order to remove the lens, access to it is created to it by a thin cut made in the lens capsule and the lens is next broken up into small pieces with a microsurgical instrument, and then these pieces are removed by means of an aspirating device.

This process takes place under microscopic observation—for example, under stereomicroscopic observation—employing a specially designed lighting device for such interventions. This lighting device presents both an illumination of the surrounding field, which is necessary for illuminating the entire operating field, as well as a red background illumination for the actual operating field limited to the pupil region of the lens, which is of decisive importance for the cataract operation. This red background illumination is derived from that fraction of illuminating light, which, after passing through the transparent media of the eye, finally strikes the retina, which appears red due to good blood perfusion, is back-scattered therefrom, and then can also be observed, of course, as an apparent red background illumination, by the surgeon by means of the operating microscope. This very characteristic red background illumination in cataract surgery is generally known in professional circles under the term "red reflex".

For an optimal recognition of details relevant for the cataract operation, a red background illumination that is as homogeneous as possible has proven to be a necessary prerequisite for the surgeon. A first requirement of the lighting device is thus to assure a homogeneity of the red reflex that is as good as possible over the entire pupil of the patient.

For complete elimination of the lens pieces of the lens of the eye which has been broken up into tiny pieces and for good recognition of transparent membranes, for example, the lens capsule, another requirement must be fulfilled, that is, a good contrasting of phase objects and in fact, this contrast should also be provided as much as possible over the entire pupil of the patient.

In the past, various solutions have already been made known in connection with the production of such red background illumination.

In U.S. Pat. No. 4,779,968 a coaxial illumination for an operating microscope is described.

According to this solution, a lighting module is provided, which can be advantageously incorporated as an additional module in existing operating microscopes. This additional module is preferably introduced on the object side underneath the principal objective of the observation device. The illumination is coupled to the axis of the microscope either with a separating plate or a separating cube.

A lighting device for an operating microscope is described in DE 4,028,605 C2, which permits a combination of zero-degree, coaxial and oblique illumination. For this purpose, the lighting device makes available movable mirror sections as well as a stationary six-degree mirror plus the respective variable diaphragms, by which means the angle of illumination and the light components of the respective lighting device can be varied. The key point of this known solution lies in the increase in contrast by means of a coaxial illumination, wherein the coaxial lighting involves an oblique illumination in the vicinity of the axis.

An ophthalmologic observation device is disclosed in DE 196 38,263 A1, in which the unavoidable corneal reflex that occurs when a patient's eye is illuminated for observation of the front segments of the eye will be suppressed. This is done by introducing a light absorber in the form of a black point in the vicinity of a luminous-field diaphragm of an otherwise known illumination.

A switchable lighting system for an ophthalmologic operating microscope is described in U.S. Pat. No. 6,011,647, in which the system can be switched between a surrounding field lighting and an optimized "red reflex" illumination during the operation. The lighting device is comprised of a light source, a collector, a luminous-field diaphragm, a tilting mirror, a field lens and a principal objective. In the case of this optimized "red reflex" lighting, the helix of the light source is then imaged or mapped in the pupil of the eye as the object plane and not the luminous-field diaphragm, as is the case with surrounding field lighting.

In EP 1,109,046 A1, finally, a lighting device is disclosed for an operating microscope, which has two reflection elements which can be moved independent of one another, by means of which both the angle of the incident light can be changed relative to the optical axis of the microscope objective and the intensity of the different light beams can be varied, independent of one another.

In the chronological sequence of the proposed solutions known from the prior art, first a "red reflex" illumination is favored under exactly zero degrees. The advantage of such a zero-degree lighting or a true coaxial lighting, respectively, lies in the production of a good homogeneity of the red reflex. The second fundamental requirement also described above of a good contrasting of the lens pieces in the lens capsule and the presentation of the capsule membrane is not sufficiently fulfilled, however, by the known lighting systems with zero-degree illumination.

A next step in the development then led to lighting in the vicinity of the axis (also referred to as coaxial illumination), in order to obtain an improvement of the contrasting. Due to the angle which varies in magnitude between the observation axis and the lighting axis, however, a shading of the red reflex that is of variable intensity is obtained, thus the disadvantage of an inhomogeneity of the red reflex. Lastly, coaxial lighting represents a compromise solution between oblique lighting and zero-degree lighting. As a consequence, the advantage of an improved contrasting leads to a deterioration in homogeneity.

The proposed solutions known from the prior art all have the disadvantage that the requirements relative to homogeneity and contrasting cannot be fulfilled simultaneously as a consequence of the inconsistencies that necessarily occur.

SUMMARY OF THE INVENTION

Starting from the named prior art, the object of the present invention is to further develop a lighting device as well as an observation device of the type named initially, in such a way that the described disadvantages can be avoided. In particular, a lighting device as well as an observation device will be provided, with which an optimal solution to the problem of practical requirements relative to homogeneity of the red reflex with a simultaneous sufficiently good contrasting of the lens pieces or membranes, can be provided in the lens capsule.

This object is solved according to the invention by the lighting device with the features according to the independent patent claim 1, the observation device with the features according to the independent patent claim 11, as well as the particular uses according to the independent patent claim 5. Other advantages, features, details, aspects and effects of the invention result from the subclaims, the description, as well as the drawings. Features and details, which are described in connection with the lighting device according to the invention, thus also apply, obviously, in connection with the observation device according to the invention and vice versa. The same is true for the particular uses.

The essence of the solution according to the invention thus first lies in a new conception of the lighting device. The present invention is thus based on the knowledge that the solution to the object according to the invention is provided by the well-defined interaction between the observation beam path and a newly conceived—at least in part—lighting beam path, and in fact with very specific optical imaging properties of the interwoven beam path of the luminous-field image and pupil mapping, thus in this case, the imaging of the light source.

A basic prerequisite for this interaction consists of the fact that relative to the optical imaging properties of the lighting beam path, substantially higher requirements must be placed on correction conditions for optical imaging errors (aberrations) that occur than is generally common in the case of conventional lighting devices.

As will be illustrated further below, with respect to the lighting device, this basic requirement can be achieved with minimal expenditure for optical components.

According to the first aspect of the invention, a lighting device is provided for an observation device, in particular for an operating microscope, with a light source and with optical components, which are provided between the light source and an objective element. The lighting device is characterized according to the invention in that the optical components are structured and arranged in such a way that the mapping of the lighting pupil is produced on the fundus of the object to be observed.

A virtual image is formed for the mapping of the lighting pupil in front of the object to be observed, thus in front of the eye of the patient. The position of this virtual image corresponds to the conjugated image site of the fundus, and thus varies with the refractive error of the eye. In particular, this virtual image then lies at the far point of the eye for an eye with correct vision.

According to the invention, the lighting device is provided for an observation device, but the invention is not limited to specific types of observation devices. For example, but not exclusively, the observation device may involve an operating microscope. Several non-exclusive examples for possible application purposes in the field of operating microscopes are described in detail in connection with the observation device according to the invention.

The lighting device has, first of all, a light source, but the invention is not limited to specific types of light sources. For example, it may be provided that the light source is formed from at least one lamp or at least one fiber-optic light guide or at least one light-emitting diode (LED). Of course, other embodiments or combinations of different embodiments are also conceivable for the light source. In the further course [of the description], the light source is described differently in the form of a fiber-optic light guide, but without limiting the invention to this concrete example.

In addition, the lighting device has an objective element. Advantageously, this element involves an objective element which is also formed as the objective element of the observation device, in particular as its principal objective. However, this is not absolutely necessary.

In addition, in the lighting device, different optical components are provided, which are arranged between the light source and the objective element.

Therefore, the optical components are formed and arranged according to the invention in such a way that a virtual image is formed in front of the object to be observed for the imaging of the lighting pupil. The "lighting pupil" involves in a causal manner the imaging or mapping of the light source, e.g., the end of the optical fiber or even also the mapping of an intermediate image of the light source, whereby this intermediate image also can still be bounded by an aperture diaphragm for control of the emergent light quantity.

The lighting device according to the invention is utilized in particular for the production of the "red reflex". Only a portion of the illumination light primarily contributes to the production of the red reflex, and it is precisely that light which strikes the corresponding light-bundle cross-sectional surfaces on the retina of the eye being examined and is back-scattered therefrom into the half-space, whereby in turn, only the fraction of the light back-scattered precisely into the corresponding observation beam cone can be perceived by the observer as the red reflex. With an identical irradiation intensity, due to the lighting, the intensity of the red reflex in the corresponding image zones is directly proportional to the degree of illumination of the light-bundle cross-sectional surfaces on the retina.

The imaging of the lighting pupil on the fundus of the eye is achieved by the configuration of the lighting device according to the invention. In particular, an equally intense, homogeneous red reflex is then obtained for all image points for the case when the illuminated image of the device pupil also lies on the retina. This homogeneity of the red reflex also does not change with partial illumination of the image of the device pupil, for example, in the case of oblique illumination or the like, but the intensity increases or decreases each time, depending on the degree of illumination.

Provision is made advantageously that the lighting device has a first optical component and a first diaphragm, wherein the diaphragm may involve, for example, a luminous-field diaphragm. This first diaphragm is then illuminated with the first optical component.

In addition, a second optical component and a second diaphragm may be provided, wherein the second diaphragm may involve, for example, an aperture diaphragm. The light source is then imaged into an intermediate image, which can be bounded by an aperture diaphragm, by means of the first and second optical components.

The invention is not limited to specific configurations for the first and second optical components. For example, the first lens component and/or the second lens component can be formed, however, as a plan convex lens.

In one embodiment, a luminous-field diaphragm is illuminated with the light source, for example, a fiber-optic light guide, with a first plan convex lens, which functions as a collector. The light source is then imaged in the aperture diaphragm with a second plan convex lens.

For example, it may be provided that the first and the second optical components are of identical form. The optical components may involve plan convex lenses, with which the light source is imaged, for example, with the imaging scale factor 1:1 in the second diaphragm, for example, the aperture diaphragm. In the solution proposed here for the lighting, an exact stigmatic imaging of the luminous-field diaphragm or of the intermediate image, which is limited only by diffraction, into the precisely allocated real or virtual conjugated image planes, respectively, is given each time, corresponding to the proposed solution. In this way an essential basic prerequisite for good homogeneity of the red reflex or contrasting of the lens pieces in the lens capsule is given.

Advantageously, an optical component of the lighting device may be formed as a cemented member consisting of at least two lens components. In this way, it can be provided that the cemented member and the second optical component are combined into an imaginary first optics part. This first optics part is formed in particular for generating an afocal beam path for the luminous-field imaging.

Then the first diaphragm, for example, the luminous-field diaphragm is disposed in the front focal point of the first optics part consisting of the second optical component or optical system, e.g., a plan convex lens and a cemented member, so that the luminous-field diaphragm is infinitely imaged by this combined optics part. Thus an afocal beam path exists in front of the objective component for the luminous-field imaging.

If the objective element also involves the principal objective of the observation device, an afocal beam path exists at the point of intersection in front of the principal objective where the illumination for the luminous-field imaging and for the observation are coupled. This is a necessary prerequisite for the circumstance that the first diaphragm (for example, the luminous-field diaphragm) is imaged by the principal objective exactly in the object plane of the observation, for example, a stereoscopic observation. If a deflecting element, which is described further below, is provided in the lighting device, the afocal beam path may exist preferably at the point of intersection where the light is coupled with the deflecting element in front of the objective element.

In another configuration, the cemented member and the objective component can be combined into an imaginary second optics part.

The intermediate image of the light source is now imaged into a virtual image in front of the object to be investigated by means of the second optics part. The intermediate image of the lighting pupil can thus be found in the front focal point of the second optics part. The position of the virtual image is conjugated to the fundus of the eye to be examined, which is in general afflicted with a refractive error. For the special case of an eye with correct vision, in which the fundus lies exactly in the focus of the eye, the virtual image of the lighting pupil must be imaged in the far point of the eye. This is achieved in that the intermediate image of the light source together with the possibly present aperture diaphragm is introduced into the front focal point of the imaginary second optics part composed of the cemented member and the objective element (which may involve, for example, the principal objective of the observation device). In this special case, this second optics part then takes over the function of the condensor in the case of classic Köhler illumination in microscopy, in which the object is illuminated with an afocal and thus parallel beam path.

Advantageously, at least one deflecting element can be provided for deflecting at least a part of the lighting beam path. Thus it is possible to beam the lighting beam path from the side, which can be of advantage, in particular, with respect to handling as well as the construction and arrangement of the lighting device inside an observation device. The deflecting element may involve, for example, a tilting mirror, a deviating prism, or the like.

In one embodiment, for example, the lighting device may be comprised of the following optical components: a light source (fiber-optic light guide), a first optical component (first plan convex lens), a first diaphragm (luminous-field diaphragm), a second optical component (second plan convex lens), a second diaphragm (aperture diaphragm), a cemented member, a deflecting element (tilting mirror), an objective element (principal objective) and an object to be observed (eye).

According to a second aspect of the invention, an observation device is provided, in particular, an operating microscope, with means for generating at least one observation beam path, having a principal objective, and with means for generating at least one lighting beam path. The observation device is hereby characterized according to the invention in that the means for generating the observation beam path are formed in order to map the image of the—stereoscopic—device pupil of the observation device in the image plane of the object to be investigated, i.e., onto the fundus, and that the means for generating the at least one lighting beam path are formed in order to map the lighting pupil in the image plane of the object to be investigated, i.e., onto the fundus, and in this way to illuminate the image of the—stereoscopic—device pupils in the image plane of the object to be investigated.

For optimal interaction of observation and lighting as the basic requirement for the solution to the problem of the red reflex, it is necessary to image both the device pupils (stereoscopic observation pupils) as well as the lighting pupil (for example, the end of the optical-fiber light guide) onto the fundus of the eye to be examined. The "device pupil" involves the point of intersection of all center or heavy beams of the imaging light bundle.

It may be provided advantageously that the means for generating the lighting beam path are formed as a lighting device according to the invention, as described above.

The means for generating the lighting beam path can thus be arranged advantageously on the side of the principal objective turned away from the object to be investigated.

It is provided in one configuration that the observation device is formed as an operating microscope. The optical system of an operating microscope basically consists of several structural elements, such as the tube, the basic body of the microscope, etc.

Additionally, it is possible in many operating microscopes to connect different added modules, such as, for example, a co-observer tube for an assistant observer, a video camera for documentation or the like.

Several assemblies can also be combined inside the base body of the microscope, such as, for example, a lighting device, a magnification device, the principal objective, or the like. The characteristic dimension for the principal objective is its focal depth, which establishes the working distance from the operating microscope to the surgical field and also has an influence on the total magnification of the microscope.

Preferably, a magnification system can be provided in the at least one observation beam path. For example, this may involve a device that changes the magnification, with which different magnifications can be adjusted. In many cases of application, a device for stepwise changing of magnification is fully sufficient. However, it is also possible to use pancratic magnification systems as the magnification system, by means of which a step-free magnification (zoom system) is possible.

In this way, it may be advantageously provided that the device pupil of the observation device, which has already been described further above, is disposed in the magnification system.

In addition, a tube element and an eyepiece element can be provided in the at least one observation beam path. The task of an eyepiece element is generally the post-magnification of the intermediate image forming in the tube, as well as perhaps compensating for the possible refractive error of the user of such a microscope.

In addition, it is advantageously provided that the object plane of the object to be investigated is formed in the front focal point of the principal objective. It is achieved in this way that the object to be investigated is imaged infinitely by the principal objective.

Advantageously, the observation device can be formed as a stereoscopic observation device, in particular as a stereomicroscope. In this case, the observation device provides two parallelly running observation beam paths.

According to a preferred embodiment, the observation device may involve a stereomicroscope according to the telescopic principle, which is essentially comprised of three optical component parts, i.e., principal objective (afocal), zoom system, and binocular telescopic device of tube and eyepiece.

The observation light bundles preferably run parallel between the individual component parts of the observation device, so that the individual component parts can be exchanged and combined as modules.

In preferred manner, a lighting device according to the invention as described above can be used in an ophthalmologic observation device, in particular in an operating microscope configured for cataract extraction. Likewise, an observation device according to the invention as described above can be used as an ophthalmologic observation device, in particular as an operating microscope configured for cataract extraction.

BRIEF DESCRIPTION OF THE DRAWINGS

The invention will now be explained in more detail based on the embodiment examples with reference to the attached drawings. Here:

Table 1 shows optical system data of a first embodiment of the lighting device according to the invention;

FIGS. 8 to 12 show various photographic representations, which clarify the influence of the lighting parameters on the "red reflex" and the contrasting function.

DETAILED DESCRIPTION OF PREFERRED EMBODIMENTS

Figure 1:
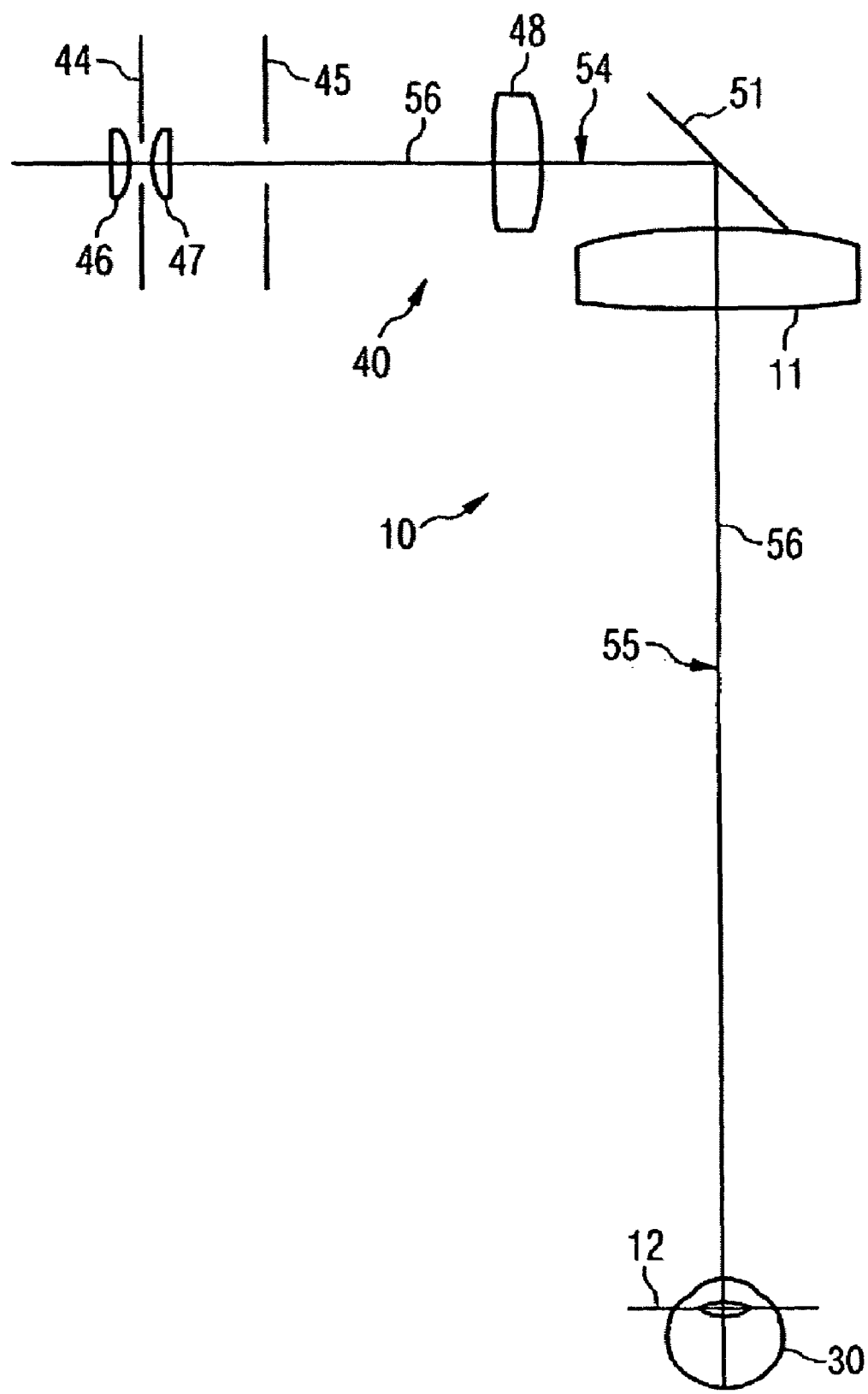
FIG. 1 shows in schematic representation an embodiment of the lighting device according to the invention.
Figure 2:
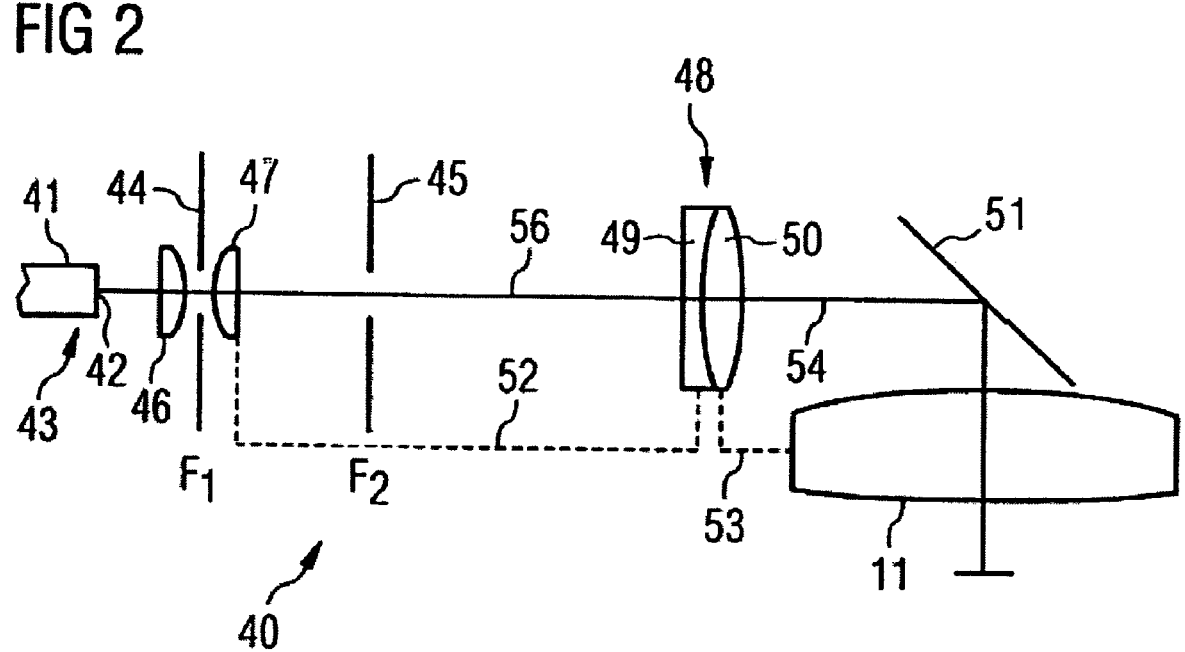
FIG. 2 shows an enlarged excerpt from the lighting device according to the invention shown in FIG. 1.

A lighting device 40, which is a component of an observation device 10, is shown in FIGS. 1 and 2. The observation device 10 involves an ophthalmologic stereo operating microscope, which is utilized for a special application in eye surgery, i.e., cataract surgery. The lighting device 40, which is explained in more detail in the following, has a light source 41, which is formed in the present example as a fiber-optic light guide. In addition, an objective element 11 is provided, which in the present case is also the principal objective of the observation device 10. A number of optical components are provided between light guide 41 and the principal objective 11. The object plane 12 of the object 30 to be investigated is formed in the front focal point of the principal objective 11. The object 30 to be investigated involves an eye.

Figure 4:
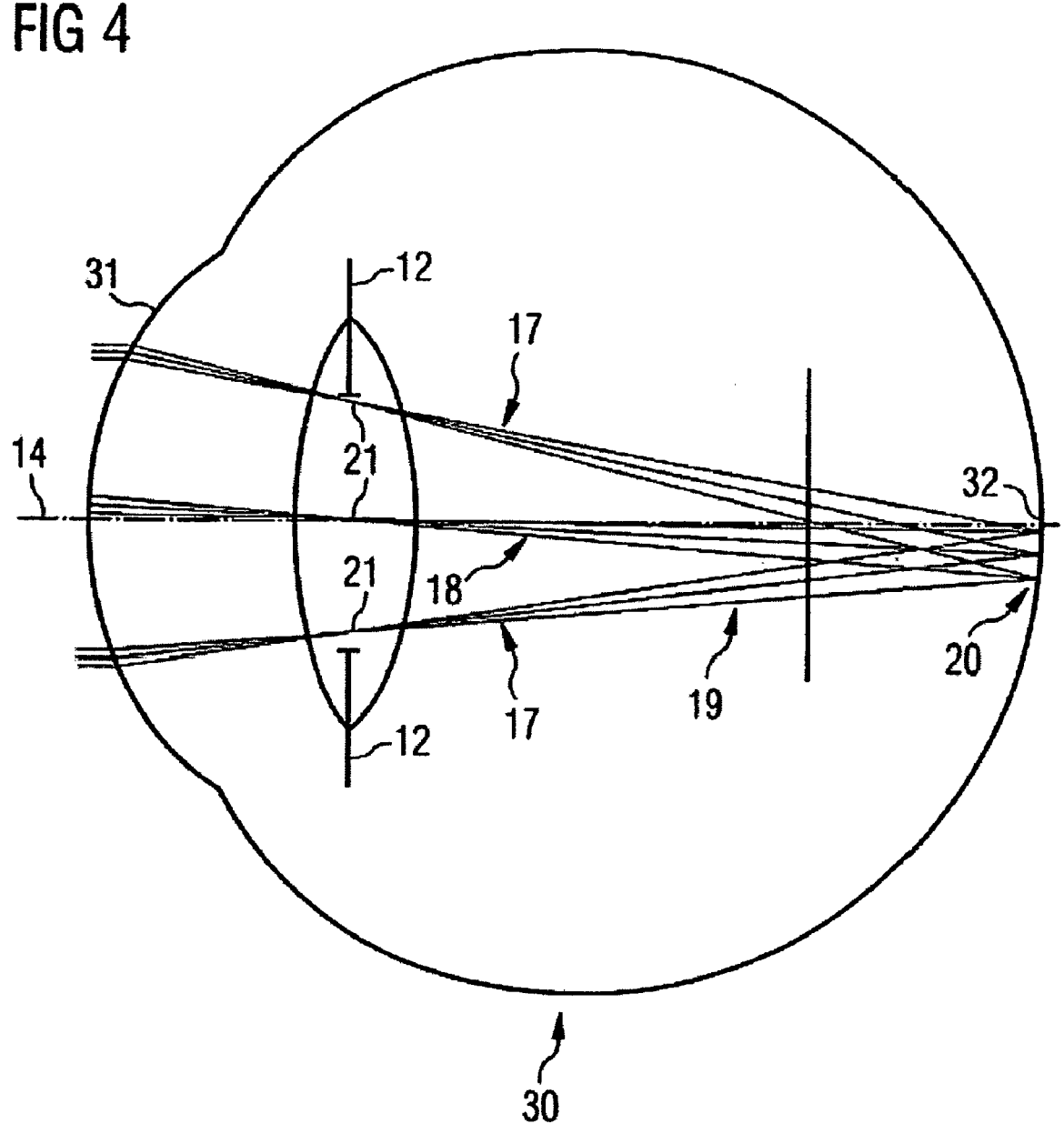
FIG. 4 shows an enlarged representation of a model eye.

For purposes of simulation, eye 30 is formed as a so-called "model eye". Experience for many years has shown that an aphacic (with defect of the lens) model eye used in experimental investigations for presenting the problem of the red reflex sufficiently well describes reality. Approximating the real situation in an aphacic human eye, the lens of the eye is removed, so that the optical effect is brought about only by the curvature of the cornea 31 (FIG. 4).

For optimal interaction of observation and lighting as the basic requirement for the solution to the problem of the red reflex, it is necessary that the observation pupils (device pupils) as well as the lighting pupil 43 (the end 42 of the optical fiber according to FIG. 2) are imaged onto the fundus 32 of the eye 30, here the retina.

The virtual image of the device pupils 15 is fixed in the specified observation optics of the operating microscope, and is set approximately 300 mm in front of the model eye 30. The ideal map of the device pupils 15 then lies in approximately the focal plane of the model eye 30.

In contrast, by suitable design of the lighting device 40 according to FIGS. 1 and 2, the map of the lighting pupil 43, thus the image of the light guide 41, can be placed precisely in the focal plane of the model eye 30. The virtual image of lighting pupil 43 then lies precisely in the far point, thus in the infinite, for this special case with respect to the model eye 30.

Figure 3:
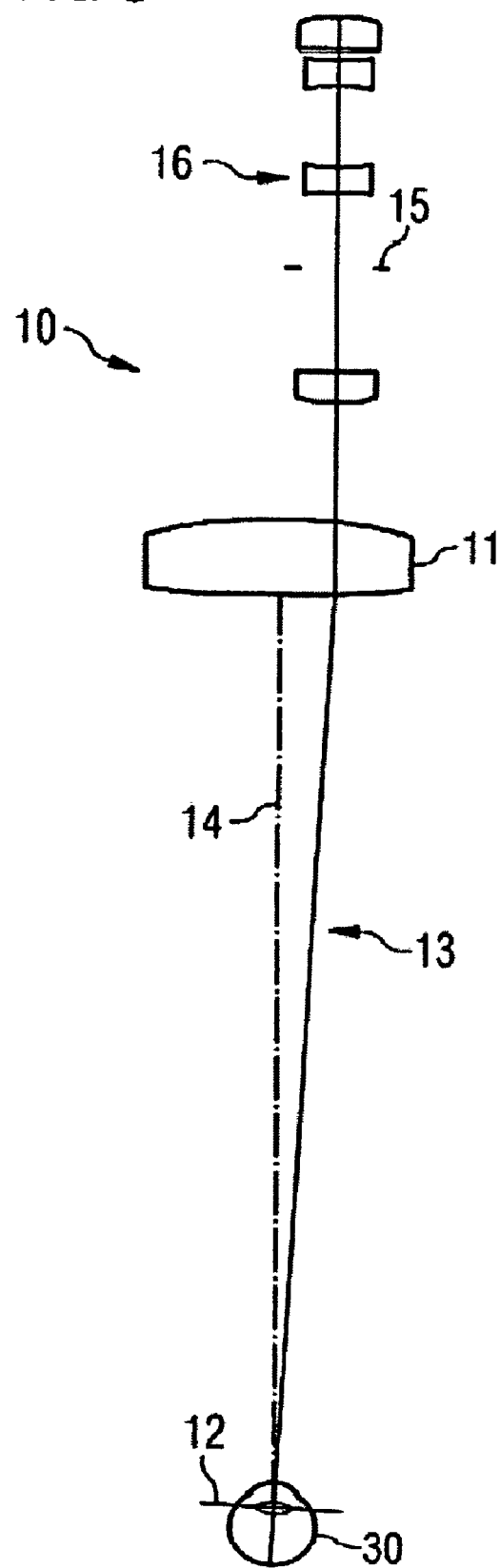
FIG. 3 shows in schematic representation the observation beam path within an observation device, in which the lighting device according to the invention can be integrated.

As is shown in FIG. 3, the optical observation device 10 corresponds to a stereomicroscope according to the telescopic principle and is essentially comprised of the three optical component parts, i.e., principal objective 11, magnification system 16 and binocular telescopic device comprised of tube and eyepiece.

The object plane 12 is found in the front focal point of the principal objective 11, so that the object 30 is infinitely imaged by the principal objective 11. Only one of the two stereoscopic observation beam paths 13 is depicted in FIG. 3. The off-centering of the axis of the magnification system 16 opposite the optical axis 14 of the principal objective 11 amounts to 11 mm, so that the total stereo base between the two stereoscopic observation beam paths is thus 22 mm.

The device pupil 15, i.e., the point of intersection of all center or primary beams of the imaging light bundles is found in magnification system 16.

The optical system of the operating microscope 10 is focused on the pupil of the eye. This means that the object plane 12 is found in the pupil of the model eye 30.

FIG. 4 shows with high magnification the course of the light bundle 17 in the model eye 30 for the observation beam path 13 corresponding to FIG. 3. Therefore, the optical axis 14 of the model eye 30 is identical to the optical axis of the principal objective 11, so that the phase object is considered at a specific stereo angle due to the stereoscopic off-centering of the observation, and the beam course in the right and left observation channels is correspondingly different, except for the common focus in the object points of the phase plane.

The determining influence of the observation beam path 13 can be particularly clearly indicated by means of the beam cross-sectional surfaces, thus, as it were, the "tracks" which imprint the light bundles 17, 13 on the retina 32.

Figure 5A:
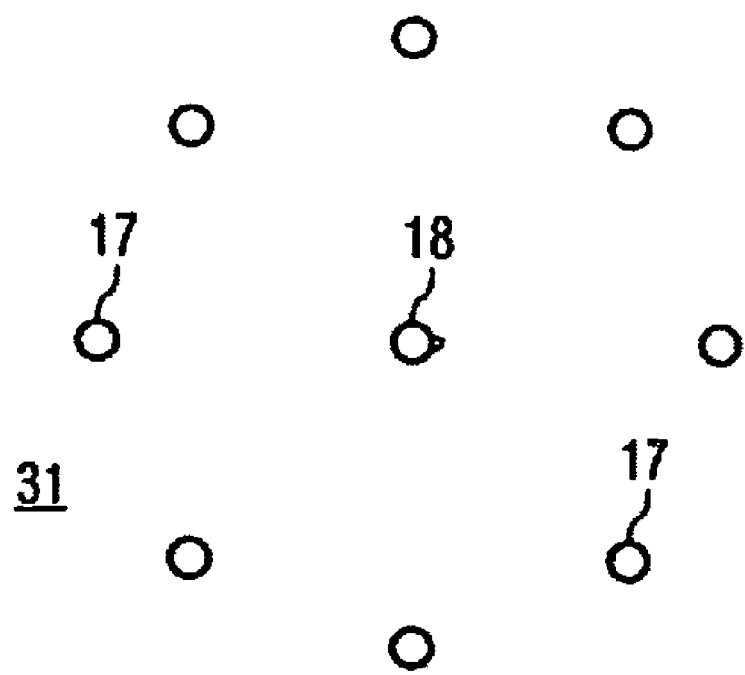
FIG. 5 shows by way of example beam cross-sectional surfaces on the cornea of the model eye according to FIG. 4.
Figure 5B:
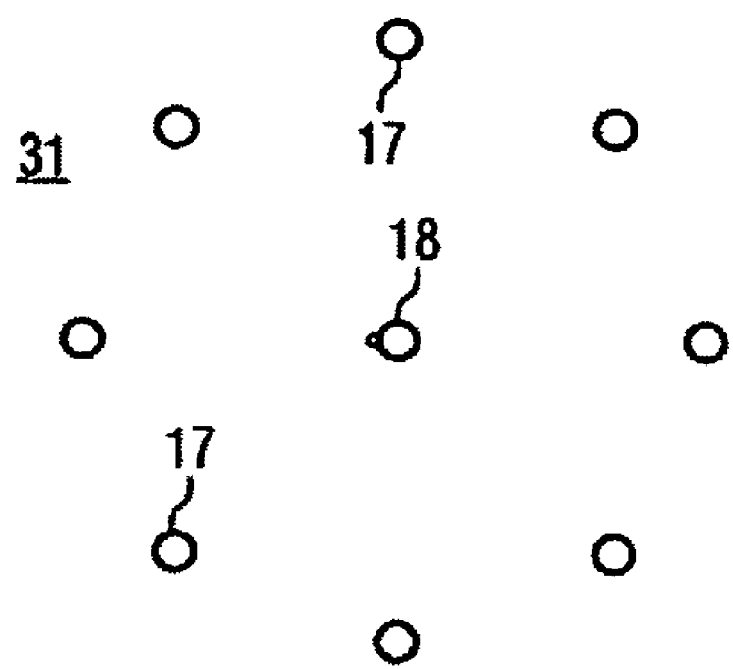

FIG. 5 shows by way of example beam cross-sectional surfaces on the cornea 31 for the center bundle 18 and at a total of eight uniformly distributed bundles over the periphery of the image field and thus the light bundles 17 bounding the entire image field, and in fact for the left (FIG. 5*a*) or right (FIG. 5*b*) observation channel.

As can be seen from FIG. 4, these cross-sectional surfaces converge toward the center of the image, whereby simultaneously their included areas become larger.

The bundle cross-sectional surfaces on the retina 32 differ now very clearly in size and relative position to one another, as a function of the refractive error of the patient's eye.

Figure 6:
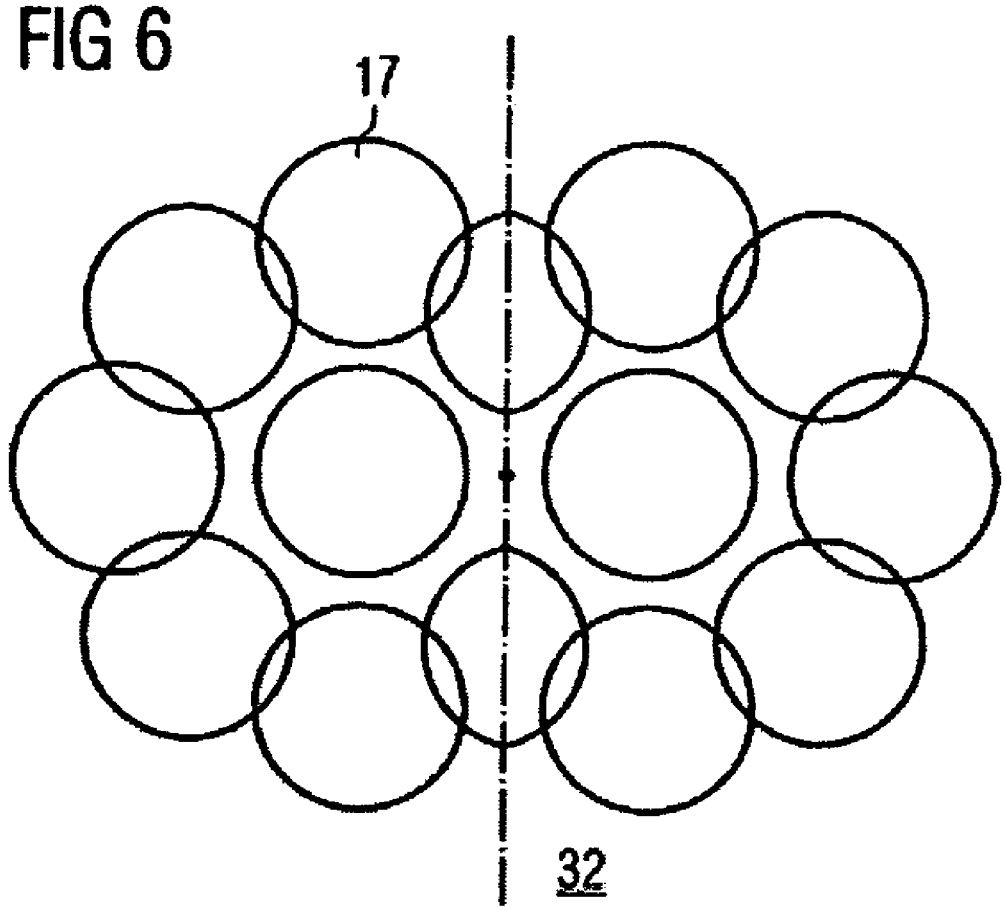
FIG. 6 shows light-bundle cross-sectional surfaces for stereo observation beam paths jointly on the retina of a model eye with a refractive error.

FIG. 6 shows these bundle cross-sectional surfaces for both stereo beam paths jointly on an imaginary retinal plane of an eye with refractive error, which lies approximately 5 mm in front of the focal plane of the model eye.

Figure 7:
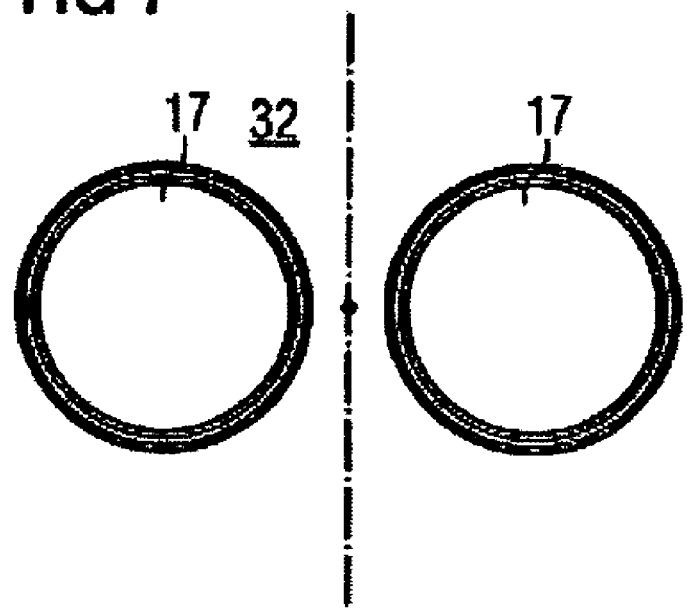
FIG. 7 shows light-bundle cross-sectional surfaces for stereo observation beam paths on the retina of a model eye, whereby, however, the cross-sectional surfaces of all light bundles come to cover over the entire image field.

As was mentioned earlier, a particular significance is ascribed to the special case in which the retina 32 lies in the focal plane of the model eye 30. In this special case, the cross-sectional surfaces of the light bundle 17 have a diameter of roughly 1.2 mm. It is of decisive importance for the homogeneity of the red reflex that in this special case, the cross-sectional surfaces of all light bundles come to cover the entire image field, as is shown in FIG. 7.

In this case, all center or primary beams of the light bundle 17 intersect as for the device pupil 15 (FIG. 3), so that the image of device pupil 15 then lies on the retina 32.

The interaction between lighting beam path 56 (FIG. 1) and observation beam path 13 (FIG. 3) can now be made clear simply on the basis of a single object point. As is represented in FIG. 4, for each object point, there is a beam cone 19, whose base 20 lies [in] the light bundle cross-sectional surfaces on the retina 32 and whose tip 21 lies in the respective object point in the considered object plane 12 containing the phase object.

Only a portion of the illumination light primarily contributes to the production of the red reflex, and it involves that light which strikes the corresponding cross-sectional surfaces of the light bundles on the retina 32 and is back-scattered there into the half-space, whereby in turn, only the fraction of the light back-scattered exactly into the corresponding beam cone 19 can be perceived by the observer as the red reflex. With an identical irradiation intensity, due to the lighting, the intensity of the red reflex in the corresponding image zones is directly proportional to the degree of illumination of the cross-sectional surfaces. In particular, an equally intense, homogeneous red reflex is then obtained for all image points for the case when the illuminated image of the device pupil 15 also lies on the retina 32. This homogeneity of the red reflex also does not change with partial illumination of the image of device pupil 15, for example in the case of oblique illumination, but the intensity increases or decreases each time, depending on the degree of illumination.

The illumination of the image of device pupil 15 on the retina 32 is now produced with a lighting device 40, which is shown in FIGS. 1 and 2 and which is comprised of the following optical components in one embodiment example, i.e., a fiber-optic light guide 41, a first optical component 46 formed as a plan convex lens, a first diaphragm 44 formed as a luminous-field diaphragm, a second optical component 47 formed as a plan convex lens, a second diaphragm 45 formed as an aperture diaphragm, a cemented member 48 comprised of two lens elements 49, 50, a deflecting element 51 in the form of a tilting mirror, the principal objective 11 as well as the model eye 30.

An enlarged representation of the components according to FIG. 1 up to the principal objective 11, which is utilized jointly by observation and illumination, is shown in FIG. 2.

A luminous-field diaphragm 44 is illuminated with the fiber-optic light guide 41, which generates the lighting beam path 56, with a first plan convex lens 46 as collector. The light guide 41 is then imaged in an intermediate image with aperture diaphragm 45 by means of a second plan convex lens 47. For example, the two plan convex lenses 46, 47 can be identical, and image the light guide 41 with the imaging scale factor 1:1 in aperture diaphragm 45.

The luminous-field diaphragm 44 preferably sits in the front focal point F1 of an imaginary first optics part 52—which is illustrated by a dashed line—which is comprised of the second plan convex lens 47 and the cemented member 48, so that the luminous-field diaphragm 44 is thus infinitely imaged by this combined optics part 52. Therefore, an afocal beam path 54 exists at the point of intersection of the illumination coupled to the tilting mirror 51 in front of the principal objective 11 for the luminous-field imaging as is also the case for the observation. This is a necessary prerequisite for the circumstance that the luminous-field diaphragm 44 is imaged by the principal objective 11 in the object plane 12 of the stereoscopic observation, namely the phase surface. A luminous-field diaphragm 44 with a diameter of approximately 2.2 mm is then imaged, for example, enlarged to about 7 mm, in the phase object plane.

In order to map the image of the fiber end 42 of fiber optic 41, thus the lighting pupil 43, onto the fundus 32 of the model eye 30, the virtual image of the lighting pupil 43 must be imaged in the image site of the model eye 30, which is conjugated to the fundus. As can be seen particularly easily, this is obtained simply for the special case of the eye with correct vision in that the intermediate image 45 of the fiber optic is introduced into the front focal point F2 of an imaginary second optics part 53—which is also illustrated by a dashed line—comprised of cemented member 48 and principal objective 11. In the general case of an eye with refractive error, this intermediate image lies at a precise distance from the front focal point F2, so that this intermediate image is then mapped by the second optics part on the virtual image plane conjugated to the retina.

For the special case of the eye with correct vision, the second optics part in turn then takes over the function of the condenser for the classic Köhler illumination in microscopy. An afocal beam path 55 thus exists in front of the eye 30 for the mapping of the lighting pupil 43. In this case, the fiber end 42 of the fiber optic 41 (lighting pupil 43), for example, is greatly reduced in size on the retina 32 of the eye with correct vision.

The optical system data of an embodiment example of the lighting device 40 according to the invention are listed in Table 1.

Numerous experimental investigations were conducted with the lighting device 40 according to the invention, which was described above. The most important experiments with respect to such experimental investigations, which are necessarily aligned to the application, will be described in detail below. First, however, in order to clarify the target direction for transferring the obtained knowledge to the respective application, a brief review of the prior investigations will be given.

The presentation of the problem, which is explained in detail within the scope of the general description, results in particular from the special application of an operating microscope in cataract surgery and essentially consists of the production of a homogeneous red reflex over the entire pupil of the eye with simultaneous good contrasting of the lens pieces and phase structures in the lens capsule. From this results the need for creating a lighting device 40, which complies with this requirement and is adapted to stereoscopic observation.

An important advantage for further development of the solution according to the invention for technical application particularly exists in the fact that this solution not only makes possible a transparent and clearly definable mathematical-optical modeling of the red reflex and the contrasting, but equally and importantly makes possible an easily discernable and clear experimental presentation of the situation characterizing the problem.

The state of development up to today has been based on the following mathematical-optical modeling of the red reflex and the contrasting, which is confirmed by practical experiments.

The red reflex arises due to the illumination of each object point of the phase surfaces in light-bundle cross-sectional surfaces on the retina, which [surfaces] are clearly allocated in the pupil of the eye. In the ideal case of the imaging or the mapping of the device pupil on the retina, these light-bundle cross-sectional surfaces come to cover all object points. For the case when the lighting pupil and thus the illumination spot are also minimized on the retina, a homogeneous illumination of the pupil of the eye and thus a homogeneous red reflex are also possible with a low level of illumination of the stereoscopic observation pupils. This is shown, for example, in FIG. 9.

The size of both the light-bundle cross-sectional surfaces as well as the illumination spot greatly depend on the refractive error of the eye, in which the length of the glass body and thus the distance of the retina from the phase surface in the pupil of the eye varies to a greater or lesser extent. In general, the illumination spot thus only covers a part of the light-bundle cross-sectional surfaces and this is done also generally with a different level of illumination. A more or less pronounced inhomogeneity of the red reflex can result therefrom. FIG. 6 supplies an illustrative explanation for this. A lateral displacement of the illumination mirror and as a consequence of this, a displacement of the illumination spot leads to an additional asymmetry of the inhomogeneous red reflex, which in turn can be clarified also on the basis of FIG. 6, and is also shown in FIG. 8.

The contrasting, thus the visualization of the lens pieces or phase objects in the lens capsule is produced primarily by illumination light bundles, whose numerical aperture, thus the angle of incidence of the light beam at the site of the phase object, is larger than the numerical aperture of the observation light bundle. In this case then, the physical-optical prerequisite for a dark-field illumination of the phase object is present, which is shown, for example, by the fact that the lighting pupil is strictly spatially separated on the retina from the two stereoscopic observer pupils (FIG. 10, right panel). This strict separation indicates a good contrasting according to the facts pointed out previously, but no red reflex, which results, for example, from FIG. 10, left panel.

A very definitive visual point is derived therefrom, however: The red reflex is primarily not the cause for the contrasting of the lens pieces and phase structures in the pupil of the eye. In the case of the contrasting, the red reflex serves secondarily as background illumination of the lens pieces and phase objects originally contrasted with dark-field illumination. Obviously, a very small fraction of the illumination light is sufficient for this background illumination according to FIG. 9. A large part of the illumination light thus lies in the region of dark-field illumination, as is shown in FIG. 9, right panel.

This knowledge of the strict separation of the illumination for the red reflex from the illumination for the contrasting, and then particularly also their additive superimposition according to FIG. 9, is a decisive factor for an optimal practical transfer of the lighting device according to the invention.

FIGS. 11 and 12 supply additional verification. The lighting pupil is directly brought to coincide therein with one of the two observation pupils. According to previous knowledge, one then expects in the illuminated observation pupil an extremely intense, homogeneous red reflex without contrasting, as is shown in FIG. 11. This illumination again operates as a pure dark-field illumination for the second observation channel, with the consequence of a good contrasting without red reflex, as is shown in FIG. 12.

| List of reference numbers | |
|---|---|
| 10 | Observation device (operating microscope) |
| 11 | Objective element (principal objective) |
| 12 | Object plane |
| 13 | Observation beam path |
| 14 | Optical axis |
| 15 | Device pupil |
| 16 | Magnification system |
| 17 | Light bundle |
| 18 | Center bundle |
| 19 | Beam cone |
| 20 | Base of the beam cone |
| 21 | Tip of the beam cone |
| 30 | Object to be investigated (eye/model eye) |
| 31 | Cornea |
| 32 | Fundus |
| 40 | Lighting device |
| 41 | Light source (fiber-optic light guide) |
| 42 | End of the light guide |
| 43 | Lighting pupil |
| 44 | First diaphragm (luminous-field diaphragm) |
| 45 | Second diaphragm (aperture diaphragm) |
| 46 | First optical component |
| 47 | Second optical component |
| 48 | Cementing member |
| 49 | Lens element |
| 50 | Lens element |
| 51 | Deflecting element (tilting mirror) |
| 52 | First optics part |
| 53 | Second optics part |
| 54 | Afocal beam path |
| 55 | Afocal beam path |
| 56 | Lighting beam path |
| F1 | Front focal point of the first optics part |
| F2 | Front focal point of the second optics part |

TABLE 1

| No. | Radius (mm) | Thickness or air distance (mm) | Glass or medium | Free diameter (mm) |
|---|---|---|---|---|
| 1 | Plan | Fiber optic light guide 17.82 | air | 12.5 |
| 2 | −10.441 | 3.5 2.0 | BK7 air | 12.5 |
| 3 | Plan | Luminous-field diaphragm 2.0 | air | |
| 4 | 10.441 | 3.5 | BK7 | 12.5 |
| 5 | Plan | 17.82 | air | |
| 6 | Plan | Aperture diaphragm 43.31 | air | 12.5 |
| 7 | 137.26 | 2.5 | NSF56 | 26.0 |
| 8 | 36.256 | 6.5 | NSSK8 | 26.0 |
| 9 | −46.639 | 33.44 | air | 26.0 |
| 10 | | Deflecting mirror 13.0 | air | |
| 11 | 120.57 | 10.5 | NFK51 | 53.0 |
| 12 | −79.719 | 5.1 | NBAF4 | 53.0 |
| 13 | −244.06 | 188.35 | air | 53.0 |
| 14 | 8.0 | Cornea Anterior chamber | air | |
| 15 | Plan | Pupil of the eye Glass body Retina | | |

The invention claimed is:

1. A lighting device for an observation device, in particular for an operating microscope, with a light source and with optical components, which are provided between the light source and an objective element,
is characterized in that
the optical components are configured and arranged in such a way that the imaging or mapping of the lighting pupil takes place on the fundus of the object to be observed, in that one of the optical components is formed as a cemented member made of at least two lens elements, in that the cemented member and the objective element are combined into an imaginary optics part, and in that the intermediate image of the lighting pupil is disposed in the front focal point of the imaginary optics part.

2. The lighting device according to claim 1, further characterized in that a first optical component and a first diaphragm are provided, and that the first diaphragm is illuminated via the first optical component.

3. The lighting device according to claim 2, further characterized in that the first optical component and/or the second optical component is formed as a plan convex lens.

4. The lighting device according to claim 2, further characterized in that the first and the second optical components are formed identically.

5. Use of a lighting device according to any one of claims 1 to 3 in an ophthalmologic observation device.

6. The lighting device according to claim 1, further characterized in that a second optical component and a second diaphragm are provided, and that the light source is imaged via the second optical component in the second diaphragm.

7. The lighting device according to claim 1, further characterized in that the first optics part is formed for generating an afocal beam path.

8. The lighting device according to claim 1, further characterized in that at least one deflecting element is provided for deflecting the lighting beam path.

9. The lighting device according to claim 1, further characterized in that the light source is formed from at least one lamp or at least one fiber-optic light guide or at least one LED.

10. The lighting device according to claim 1, further characterized in that the objective element is also formed as an objective element of an observation device.

11. An observation device with means for producing at least one observation beam path, having a principal objective, and with means for producing at least one lighting beam path,
is characterized in that
the means for producing the observation beam path are formed in order to map the image of the device pupils of the observation device on the fundus of the object to be investigated, the device pupils being the location where the primary and the center rays come to focus, and
that the means for producing the at least one lighting beam path are formed, in order to image the lighting pupil on the fundus of the object to be investigated, and in this way to illuminate the image of the device pupils on the fundus of the object to be investigated.

12. The observation device according to claim 11, further characterized in that the means for producing the lighting beam path are formed as a lighting device with a light source and with optical components, which are provided between the light source and an objective element, wherein the optical components are configured and arranged in such a way that the imaging or mapping of the lighting pupil takes place on the fundus of the object to be observed.

13. The observation device according to claim 11, further characterized in that the means for producing the lighting beam path are disposed on the side of the principal objective turned away from the object to be investigated.

14. The observation device according to claim 11, further characterized in that at least one magnification system is provided in the at least one observation beam path.

15. The observation device according to claim 14, further characterized in that the device pupil of the observation device is provided in the magnification system.

16. The observation device according to claim 11, further characterized in that a tube element and/or an eyepiece element is/are provided in the at least one observation beam path.

17. The observation device according to claim 11, further characterized in that the object plane of the object to be investigated is formed in the frontmost focal point of the principal objective.

18. The observation device according to claim 11, further characterized in that this is formed as a stereoscopic observation device.

19. The observation device according to claim 11, further characterized in that this is formed as an ophthalmologic observation device.

20. A lighting device for an observation device, in particular for an operating microscope, with a light source and with optical components, which are provided between the light source and an objective element,
is characterized in that
the optical components are configured and arranged in such a way that the imaging or mapping of the lighting pupil takes place on the fundus of the object to be observed, in that one of the optical components is formed as a cemented member made of at least two lens elements, in that the cemented member and a second optical component are combined into an imaginary first optics part, and in that a first diaphragm is disposed in the front focal point of the imaginary first optics part.

21. A lighting device for an observation device, in particular for an operating microscope, with a light source and with optical components, which are provided between the light source and an objective element,
is characterized in that
the optical components are configured and arranged in such a way that an intermediate part of the lighting pupil takes place on the fundus of the object to be observed.

22. A lighting device for an observation device, in particular for an operating microscope, with a light source and with optical components, which are provided between the light source and an objective element,
is characterized in that
the optical components are configured and arranged in such a way that the imaging or mapping of the lighting pupil takes place on the fundus of the object to be observed.

* * * * *